United States Patent [19]

Witzeman et al.

[11] Patent Number: 5,028,682

[45] Date of Patent: Jul. 2, 1991

[54] OXIME-BLOCKED POLYSICYANATES AND POLYESTER AND POWDER COATING COMPOSITIONS CONTAINING SUCH OXIDE-BLOCKED POLYISOCYANATES

[75] Inventors: J. Stewart Witzeman; Glenn C. Jones, both of Kingsport, Tenn.

[73] Assignee: Eastman Kodak Company, Rochester, N.Y.

[21] Appl. No.: 375,079

[22] Filed: Jul. 3, 1989

[51] Int. Cl.$^5$ .............................................. C08G 18/80
[52] U.S. Cl. .................................. 528/45; 428/423.1; 428/425.8
[58] Field of Search ............. 528/45; 428/423.1, 425.8

[56] References Cited

U.S. PATENT DOCUMENTS

| 3,375,539 | 3/1983 | McBride et al. | 528/288 |
| 3,694,389 | 9/1972 | Levy | 260/23 |
| 3,857,818 | 12/1974 | Frizelle | 260/77.5 |
| 3,933,759 | 1/1976 | Hoeschele | 260/77.5 |
| 4,046,744 | 9/1977 | Jenkins | 260/77.5 |

OTHER PUBLICATIONS

McBride, J. Oil Col. Chem. Assoc., 1982, 65, 257.
Pappas et al, Proceedings of Water-Borne and Higher-Solids Coatings Symposium, Feb. 1986, p. 146.

Primary Examiner—Maurice J. Welsh
Attorney, Agent, or Firm—Bernard J. Graves, Jr.; J. Frederick Thomsen; William P. Heath, Jr.

[57] ABSTRACT

Disclosed are certain ketoxime-blocked polyisocyanates and polyester compositions containing the ketoxime-blocked polyisocyanates. Also disclosed are thermosetting powder coating compositions comprising one or more polyesters and at least one of the ketoxime-blocked polyisocyanates and articles coated with the powder coating compositions.

23 Claims, No Drawings

OXIME-BLOCKED POLYSICYANATES AND POLYESTER AND POWDER COATING COMPOSITIONS CONTAINING SUCH OXIDE-BLOCKED POLYISOCYANATES

This invention concerns novel ketoxime-blocked polyisocyanates and polyester compositions containing the novel oxime-blocked polyisocyanates. This invention also concerns novel powder coating compositions comprising one or more polyesters and one of the oxime-blocked polyisocyanates and articles coated with the novel powder coating compositions.

Plastic materials used in the manufacture of powder coatings are classified broadly as either thermosetting or thermoplastic. In the application of thermoplastic powder coatings, heat is applied to the coating on the substrate to melt the particles of the powder coating and thereby permit the particles to flow together and form a smooth coating.

Thermosetting coatings, when compared to coatings derived from thermoplastic compositions, generally are tougher, more resistant to solvents and detergents, have better adhesion to metal substrates and do not soften when exposed to elevated temperatures. Furthermore, thermosetting powder coating compositions usually are easier to manufacture due to the relatively simple procedures required for grinding the thermosetting polymeric material of the coating compositions. However, the curing of thermosetting coatings has created problems in obtaining coatings which have, in addition to the above-stated desirable characteristics, good smoothness and flexibility. Coatings prepared from thermosetting powder compositions, upon the application of heat, may cure or set prior to forming a smooth coating, resulting in a non-uniform and/or textured finish referred to as an "orange peel" surface. Such a coating surface or finish lacks the gloss and luster of coatings typically obtained from thermoplastic compositions. The "orange peel" surface problem has caused thermosetting coatings to be applied from organic solvent systems which are inherently undesirable because of the environmental and safety problems occasioned by the evaporation of the solvent system. Solvent-based coating compositions also suffer from the disadvantage of relatively poor percent utilization, i.e., in some modes of application, only 60 percent or less of the solvent-based coating composition being applied contacts the article or substrate being coated. Thus, a substantial portion of solvent-based coatings can be wasted since that portion which does not contact the article or substrate being coated obviously cannot be reclaimed.

In addition to exhibiting good gloss, impact strength and resistance to solvents and chemicals, coatings derived from thermosetting coating compositions must possess good to excellent flexibility. For example, good flexibility is essential for powder coating compositions used to coat sheet (coil) steel which is destined to be formed or shaped into articles used in the manufacture of various household appliances and automotive parts wherein the sheet metal is flexed or bent at various angles.

Another characteristic or property which powder coating compositions must possess is storage stability, i.e., the ability of the powder coating composition to remain in a finely divided, free-flowing state free from agglomeration over prolonged periods of time prior to the use of the composition. Significant agglomeration, i.e., caking or lumping, presents severe problems in the application of powder coatings and can require regrinding of the composition, a requirement that can be economically unfeasible. Semi-crystalline polyesters have been proposed for powder coating compositions to impart storage stability to the compositions. These semi-crystalline polyesters typically have a glass transition temperature of less than 55° C. and as a result thereof produce coatings which are relatively soft.

Yet another desirable characteristic of powder coating compositions is rapid curing or cross-linking of the composition after it has been applied to an article. Thus, powder coating compositions which cure at a lower temperature permit the use of lower curing oven temperatures and/or faster line speeds in the preparation of various types of coated articles.

We have discovered that powder coating compositions comprising certain novel, oxime-blocked polyisocyanates and certain polyesters containing free hydroxyl groups possess excellent storage stability, may be cured at relatively low temperatures and produce coatings which exhibit an excellent combination of properties such as flexibility, impact strength and chemical resistance.

The use of oxime-blocked isocyanates, particularly 2-butanone oxime, in coatings has been described in the literature. U.S. Pat. No. 3,694,389 discloses the use of oxime-blocked isocyanates, e.g. oxime-blocked 2-isocyanatoethyl caproate, with acrylic resins in solvent-borne coatings. U.S. Pat. No. 3,857,818 describes the use of oxime-blocked isocyanates in polyester powder coating compositions. Oxime-blocked isocyanates disclosed include the reaction product of 2-butanone oxime with methylene-bis(4,4,-cyclohexylisocyanate) and isophorone diisocyanate, i.e., 3-isocyanatomethyl 3,5,5-trimethylcyclohexylisocyanate. This last-mentioned patent also discloses the use of glycol or diamine extenders to permit the preparation of physically-solid compounds for use as cross-linking agents in powder coating compositions.

U.S. Pat. No. 3,933,759 discloses the preparation and use of oxime-blocked isocyanates which have been functionalized with polymeric glycols. The disclosed compounds are prepared by partially blocking the polyisocyanates and then reacting the intermediates with a polymeric glycol. U.S. Pat. No. 4,046,744 discloses the use of oxime-blocked isocyanates with oxazolidine-containing materials to produce solvent-borne coating formulations. U.S. Pat. No. 4,375,539 discloses the use of acetone oxime-blocked 1,4-cyclohexane-bis(methylisocyanate) in combination with polyester resins in powder coating compositions.

The use of 2,6-dimethyl-4-heptanone oxime as a blocking group for 1,4-cyclohexane-bis(methylisocyanate) is disclosed by McBride, J. Oil Coul. Chem. Assoc., 1982, 65, 257. Papas et al, Proceedings of Water-Borne and Higher-Solids Coatings Symposium, Feb. 1986, p. 146, have mentioned the use of 2,4-dimethyl-3-pentanone oxime, as well as 2-butanone oxime and acetone oxime, in model studies. The use of benzophenone oxime and other oximes with aromatic mono- and diisocyanates is described by Levine et al, J. Org. Chem., 37, 1500, 2455 (1972).

The novel oxime-blocked polyisocyanates provided by this invention are the reaction product of an oxime selected from 2,4-dimethyl-3-pentanone oxime and 2,6-dimethyl-4-heptanone oxime and a polyisocyanate selected from the trimer of isophorone diisocyanate, i.e., mixed isomers of triisocyanato cyclic isocyanurate compounds described in U.S. Pat. No. 4,150,211, methylene-bis(4,4-cyclohexylisocyanate) and 1,3- and 1,4-bis(1-isocyanato-1-methylethyl)benzene. The oxime-blocked polyisocyanates derived from the trimer of isophorone diisocyanate are constituted primarily of a mixture of isomers of the isocyanurate trimer of 3-isocyanatomethyl-3,5, 5-trimethylcyclohexylisocyanate, the three isocyanato groups of which have been converted to groups having the formula

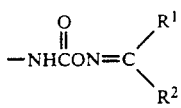

wherein $R^1$ and $R^2$ each is isopropyl or isobutyl. The oxime-blocked polyisocyanates derived from methylene-bis(4,4,-cyclohexylisocyanate) and 1,3- and 1,4-bis(1-isocyanato-1 methylethyl)benzene have the structures:

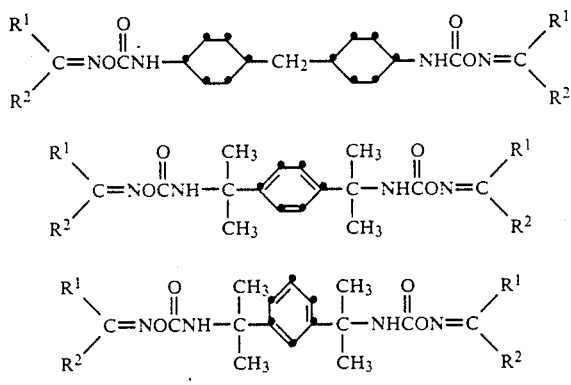

wherein $R^1$ and $R^2$ each is isopropyl or isobutyl.

The novel, oxime-blocked polyisocyanates, when used in combination with the hydroxyl-containing polyesters described hereinafter, react with and thus cross-link the polyesters at temperatures significantly lower, e.g., from about 50° to 75° F. lower, than temperatures typically required to effect cross-linking of powder coating compositions based on other polyesters and/or cross-linking agents. The oxime-blocked polyisocyanates provided by our invention may be prepared according to known procedures such as those described hereinbelow. The novel polyester compositions of our invention comprise a blend of:

(1) a semi-crystalline polyester having a glass transition temperature of not more than 50° C., a number average molecular weight of about 500 to 10,000, a hydroxyl number of about 5 to 200 and an inherent viscosity of about 0.1 to 0.5 and comprised of:
  (a) diacid residues comprised of at least 80 mole percent of terephthalic acid residues, 1,4-cyclohexanedicarboxylic acid residues, 1,3-cyclohexanedicarboxylic acid residues or a mixture thereof; and
  (b) diol residues comprised of (i) about 50 to 100 mole percent of residues having the formula —O(CH$_2$)$_n$O— wherein n is about 6 to 12 and (ii) about 0 to 50 mole percent of 2,2-dimethyl-1,3-propanediol residues, provided that at least 90 mole percent of the diol residues are residues having the formula —O(CH$_2$)$_n$O— and 2,2-dimethyl-1,3-propanediol residues; and (2) a cross-linking effective amount of one or more of the novel oxime-blocked polyisocyanates described above.

The semi-crystalline polyester has a discernable crystallization or melting point by differential scanning calorimetry (DSC). In addition to the residues specified hereinabove, the semi-crystalline polyester may contain minor amounts, e.g., up to 10 mole percent based on a total diol residue content of 100 mole percent and a total diacid residue content of 100 mole percent, of other diacid and diol residues such as the residues of ethylene glycol, propylene glycol, 1,3-propanediol, 2,4-dimethyl-2-ethylhexane-1,3-diol, 2,2-dimethyl-1,3-propanediol, 2-ethyl-2-butyl-1,3-propanediol, 2-ethyl-2-isobutyl-1,3-propanediol, 1,3-butanediol, 1,5-pentanediol, 1,6hexanediol, thiodiethanol, 1,2-, 1,3- and 1,4-cyclohexanedimethanol, 2,2,4,4-tetramethyl-1,3-cyclobutanediol, 1,4-xylylenediol and residues of succinic, glutaric, adipic, azelaic, sebacic, fumaric, maleic, itaconic, phthalic and/or isophthalic acids. However, the semi-crystalline polyester normally consists essentially of residues of terephthalic acid, 1,4-cyclohexanedicarboxylic acid, 1,3-cyclohexanedicarboxylic acid and 2,2-dimethyl-1,3-propanediol and the C-6 to C-12 diol residues described above. The 1,4-cyclohexanedicarboxylic acid or its dialkyl ester used in the preparation of the polyesters may be the trans isomer, the cis isomer or a mixture of such isomers. Preferably, the cis:trans ratio is in the range of about 35:65 to about 65:35.

The preferred semi-crystalline polyester has a glass transition temperature of less than 20° C., a melting point of about 90° to 140° C., a hydroxyl number of about 8 to 60 and an inherent viscosity of about 0.1 to 0.4 and is comprised of
(a) diacid residues consisting essentially of about 50 to 100 mole percent terephthalic acid residues and 0 to about 50 mole percent of 1,4-cyclohexanedicarboxylic acid residues, 1,3-cyclohexanedicarboxylic acid residues or a mixture thereof; and
(b) diol residues consisting essentially of about 70 to 100 mole percent of residues having the formula —O(CH$_2$)$_n$O— wherein n is about 6 to 12 and about 0 to 30 mole percent 2,2-dimethyl-1,3propanediol residues. The semi-crystalline polyesters which are especially preferred are: (1) a polyester wherein the diacid residues consist essentially of about 85 to 95 mole percent terephthalic acid residues and about 5 to 15 mole percent 1,4-cyclohexanedicarboxylic acid residues and the diol residues consist essentially of 1,6-hexanediol residues; (2) a polyester wherein the diacid residues consist essentially of at least 95 mole percent terephthalic acid residues and the diol residues consist essentially of about 80 to 90 mole percent 1,6-hexanediol residues and about 10 to 20 mole percent 2,2-dimethyl-1,3-propanediol residues; and (3) a polyester wherein the diacid residues consist essentially of at least 95 mole percent terephthalic acid residues and the diol residues consist essentially of about 70 to 85 mole percent 1,10-decanediol residues and about 10 to 30 mole percent 2,2-dimethyl-1,3-propanediol residues.

The polyester compositions provided by our invention include blends of the described semi-crystalline polyester with one or more amorphous polyesters containing free hydroxyl groups. These blends may contain up to about 70 weight percent, preferably about 20 to 50 weight percent, based on the weight of the polyester blend, of the amorphous polyester. The amorphous polyester typically has a glass transition temperature of greater than 40° C., a hydroxyl number of about 5 to 200 and an inherent viscosity of about 0.1 to 0.5.

Both the semi-crystalline and the amorphous polyesters may be produced using well-known polycondensation procedures employing an excess of glycol to obtain a polymer having the specified hydroxyl number. The glycol residues of the amorphous polyester component may be derived from a wide variety and number of aliphatic, alicyclic and alicyclic-aromatic glycols or diols containing from 2 to about 10 carbon atoms. Examples of such glycols include ethylene glycol, propylene glycol, 1,3-propanediol, 2,4-dimethyl-2-ethylhexane-1,3-diol, 2,2-dimethyl-1,3-propanediol, 2-ethyl-2-butyl-1,3-propanediol, 2-ethyl-2-isobutyl-1,3-propanediol, 1,3-butanediol, 1,4-butanediol, 1,5-pentanediol, 1,6-hexanediol, thiodiethanol, 1,2 , 1,3- and 1,4-cyclohexanedimethanol, 2,2,4,4-tetramethyl 1,3-cyclobutanediol, 1,4-(xylylenediol and the like.

The dicarboxylic acid residues of the amorphous polyester may be derived from various aliphatic, alicyclic, aliphatic-alicyclic and aromatic dicarboxylic acids containing about 4 to 10 carbon atoms or ester-forming derivatives thereof such as dialkyl ester and/or anhydrides. Succinic, glutaric, adipic, azelaic, sebacic, fumaric, maleic, itaconic, 1,3- and 1,4-cyclohexanedicarboxylic, phthalic, isophthalic and terephthalic are representative of the dicarboxylic acids from which the diacid residues of the amorphous polyester may be derived. A minor amount, e.g., up to 10 mole percent, of the glycol and/or diacid residues may be replaced with branching agents, e.g., trifunctional residues derived from trimethylolethane, trimethylolpropane and trimellitic anhydride.

The preferred amorphous polyester component of the polyester blend provided by this invention has a Tg greater than 55° C., a hydroxyl number in the range of about 25 to 80, an acid number of not more than 15 and an inherent viscosity of about 0.15 to 0.4. As used herein, the term "amorphous" refers to a polyester which exhibits no, or only a trace of, crystallization or melting point as determined by differential scanning calorimetry (DSC). The amorphous polyester component preferably is comprised of (1) diacid residues of which at least 50 mole percent are terephthalic acid residues, (2) diol residues of which at least 50 mole percent are derived from 2,2-dimethyl-1,3-propanediol (neopentyl glycol) and (3) up to 10 mole percent, based on the total moles of (1), (2) and (3), of trimethylolpropane or trimellitic acid residues. These preferred amorphous polyesters are commercially available, e.g., under the names AZS 50 Resin, Rucote 107 Resin, Cargill Resin 3000 and Cargill Resin 3016, and/or can be prepared according to the procedures described in U.S. Pat. Nos. 3,296,211, 3,842,021, 4,124,570 and 4,264,751 and Published Japanese Patent Applications (Kokai) 73-05,895 and 73-26,292. The most preferred amorphous polyester consists essentially of terephthalic acid residues, 2,2-dimethyl-1,3-propanediol residues and up to 15 mole percent, based on the total moles of trimethylolpropane and 2,2-dimethyl-1,3-propanediol residues, of trimethylolpropane residues and having a Tg of about 55° to 65° C., a hydroxyl number of about 35 to 65, an acid number of less than 10 and an inherent viscosity of about 0.1 to 0.25.

The cross-linking effective amount of the oxime-blocked polyisocyanate cross-linking compound present in the compositions of our invention can be varied significantly depending on several factors such as the properties and characteristics of the particular semi-crystalline polyester employed and, if present, the amorphous polyester employed, the degree of pigment loading, the properties required of the coatings to be prepared from the compositions, etc. Typically, the amount of the oxime-blocked polyisocyanate which will effectively cross-link the hydroxy-containing polymer or polymers to produce coatings having a good combination of properties is in the range of about 5 to 35 weight percent, preferably 8 to 25 weight percent, based on the total weight of the polyester or polyesters and the cross-linking compound.

The powder coating compositions of our invention may be prepared from the compositions described herein by dry-mixing and then melt-blending the semi-crystalline polyester, the amorphous polyester (if used) and the oxime-blocked polyisocyanate compound, along with other additives commonly used in powder coatings, and then grinding the solidified blend to a particle size, e.g., an average particle size in the range of about 10 to 300 microns, suitable for producing powder coatings. For example, the ingredients of the powder coating composition may be dry blended and then melt blended in a Brabender extruder at 90° to 130° C., granulated and finally ground. The melt blending should be carried out at a temperature sufficiently low to linking compound and thus avoid premature cross-linking. However, the temperature must be sufficiently high to effect adequate mixing of all of the components. When using a blend of polyesters, the exposure of the oxime-blocked polyisocyanate to elevated temperatures can be minimized by blending the semi-crystalline polyester and the amorphous polyester prior to the incorporation therein of the blocked polyisocyanate compound.

Typical of the additives which may be present in the powder coating compositions include benzoin, used to reduce entrapped air or volatiles, flow aids or flow control agents which aid the formation of a smooth, glossy surface, catalysts to promote the cross-linking reaction between the isocyanate groups of the cross-linking agent and the hydroxyl groups on the polymers, stabilizers, pigments and dyes. Although it is possible to cure or cross-link the composition without the use of a catalyst, it is usually desirable to employ a catalyst to aid the cross-linking reaction, e.g., in an amount of about 0.05 to 2.0 weight percent cross-linking catalyst based on the total weight of the semi-crystalline polyester, the amorphous polyester, if present, and the cross-linking agent. Suitable catalysts for promoting the cross-linking include organo-tin compounds such as dibutyltin dilaurate, dibutyltin dimaleate, dibutyltin oxide, dimethyltin dichloride, stannous octanoate and similar compounds. The organo-tin catalysts may be used in combination with an amine, e.g., tertiary amines such as 1,4-diazabicyclo[2.2.2]octane, triethylamine, tributylamine, quinuclidine and the like.

The powder coating compositions preferably contain a flow aid, also referred to as flow control or leveling agents, to enhance the surface appearance of cured coatings of the powder coating compositions. Such flow aids typically comprise acrylic polymers and are available from several suppliers, e.g., Modaflow from Monsanto Company and Acronal from BASF. Other flow control agents which may be used include Modarez MFP available from Synthron, EX 486 available from Troy Chemical, BYK 360P available from BYK Mallinkrodt and Perenol F-30-P available from Henkel. A specific flow aid is an acrylic polymer having a molecular weight of about 17,000 and containing 60 mole percent 2-ethylhexyl methacrylate residues and about 40 mole percent ethyl acrylate residues. The amount of flow aid present may be in the range of about 0.5 to 4.0 weight percent, based on the total weight of the semi-crystalline polyester, the amorphous polyester, if present, and the cross-linking agent.

The powder coating compositions may be deposited on various metallic and non-metallic substrates by known techniques for powder deposition such as by means of a powder gun, by electrostatic deposition or by deposition from a fluidized bed. In fluidized bed sintering, a preheated article is immersed into a suspension of the powder coating in air. The particle size of the powder coating composition normally is in the range of 60 to 300 microns. The powder is maintained in suspension by passing air through a porous bottom of the fluidized bed chamber. The articles to be coated are preheated to about 250° to 400° F. (about 121° to 205° C.) and then brought into contact with the fluidized bed of the powder coating composition. The contact time depends on the thickness of the coating that is to be produced and typically is from 1 to 12 seconds. The temperature of the substrate being coated causes the powder to flow and thus fuse together to form a smooth, uniform, continuous, uncratered coating. The temperature of the preheated article also affects cross-linking of the coating composition and results in the formation of a tough coating having a good combination of properties. Coatings having a thickness between 200 and 500 microns may be produced by this method.

The powder coating compositions also may be applied using an electrostatic process wherein a powder coating composition having a particle size of less than 100 microns, preferably about 15 to 50 microns, is blown by means of compressed air into an applicator in which it is charged with a voltage of 30 to 100 kV by high-voltage direct current. The charged particles then are sprayed onto the grounded article to be coated to which the particles adhere due to the electrical charge thereof. The coated article is heated to melt and cure the powder particles. Coating of 40 to 120 microns thickness may be obtained.

Another method of applying the powder coating compositions is the electrostatic fluidized bed process which is a combination of the two methods described above. For example, annular or partially annular electrodes are mounted over a fluidized bed so as to produce an electrostatic charge such as 50 to 100 kV. The article to be coated, either heated, e.g., 250° to 400° F., or cold, is exposed briefly to the fluidized powder. The coated article then can be heated to effect cross-linking if the article was not preheated to a temperature sufficiently high to cure the coating upon contact of the coating particles with the article.

The powder coating compositions of this invention may be used to coat articles of various shapes and sizes constructed of heat-resistant materials such as glass, ceramic and various metal materials. The compositions are especially useful for producing coatings on articles constructed of metals and metal alloys, particularly steel articles.

The compounds, compositions and coatings of our invention are further illustrated by the following examples.

EXAMPLE 1

The trimer of isophorone diisocyanate (70.28 g-100% solids; Hüls IPDI T 1890) was warmed in a dry, 500 mL, 3-neck flask equipped with a nitrogen inlet, a mechanical stirrer, an addition funnel and a thermocouple-regulated heating mantle to 110° C., at which temperature it melted. The melt was stirred slowly while 2,6-dimethyl-4-heptanone oxime (50.98 g) was added slowly over a 20.minute period. After 20 minutes the reaction product was poured from the flask and allowed to solidify. The oxime-blocked polyisocyanate obtained had a glass transition temperature (Tg) of greater than 50° C. and contained less than 0.3 mole percent free isocyanato groups as determined by infrared spectroscopy.

EXAMPLE 2

To a dry, nitrogen-blanketed, 300 mL, 3-neck flask equipped with a magnetic stirrer and a thermocouple-regulated heating mantle was charged dry ethyl acetate (100 mL) and isophorone diisocyanate trimer (97.00 g; Hüls IPDI T 1890). The mixture was warmed to 45° C. to dissolve the solid polyisocyanate. To the stirred solution was added 2,4-dimethyl-3-pentanone oxime (57.0 g), resulting in an exotherm to 70° C. The reaction mixture was heated at 45° C. with stirring over a weekend (ca. 60 hours) after which no free isocyanato groups remained as shown by infrared spectroscopy. The reaction mixture was transferred to a 1-neck, round-bottom flask and the reaction flask was rinsed with 20-30 mL ethyl acetate which was added to the mixture transferred. The ethyl acetate was removed on a rotary evaporator using a bath temperature of 25° to 35° C. The resulting amorphous solid was chipped in the flask to which was then attached a Kugelrohr apparatus. The reaction product was dried for 20 hours at 1-2 torr with agitation and then at 35° C. at 1-2 torr for 8 hours. The oxime-blocked polyisocyanate, which had a Tg of greater than 50° C., was cooled to room temperature, chipped and bottled.

EXAMPLE 3

To a dry, 2 L, 3-neck flask equipped with a magnetic stirrer, an addition funnel, a nitrogen inlet and a thermometer was charged 2,6-dimethyl-4-heptanone oxime (216.53 g), triethylamine catalyst (4.5 mL) and methylene chloride (200 mL). A solution of methylenebis(4-cyclohexylisocyanate) (166 mL; Desmondur W) in methylene chloride (75 mL) was added slowly to keep the reaction temperature below 35° C. The reaction mixture was stirred overnight and then was concentrated in vacuo and recrystallized from a mixture of petroleum ether and acetone. Field desorption mass spectrometry showed that the oxime-blocked polyisocyanate thus obtained had a molecular weight of 576.

The powder coating compositions described in Examples 4 to 15 and 19 to 21, and Comparative Examples 1 to 5 and 8 were prepared by combining the ingredients and melt-mixing them in a Banbury mixer at 80° C. for 5 minutes followed by granulation, grinding in a Bantam mill to which a stream of liquid nitrogen was fed and classification through a 200 mesh screen on an Alpine sieve. The finely divided, powder coating compositions had an average particle size of about 50 microns.

The powder coating compositions described in Examples 16 to 18 and Comparative Examples 6 and 7 were prepared by combining the components of each formulation and mixing the formulation in and extruding it from a twin-screw melt extruder with the first zone maintained at 120°±2° C. and the second at 130°±2° C. The resulting extrudate then was granulated and ground to a fine powder according to the procedure described above.

The semi-crystalline polyesters employed had the following compositions and characteristics:

I. Polyester of diacid residues consisting of 100 mole percent terephthalic acid residues and diol residues consisting of 15 mole percent 2,2-dimethyl-1,3-propanediol and 85 mole percent 1,6-hexanediol residues and having an inherent viscosity of 0.28 and a hydroxyl number of 32.

II. Polyester of diacid residues consisting of 100 mole percent terephthalic acid residues and diol residues consisting of 15 mole percent 2,2-dimethyl-1,3-propanediol and 85 mole percent 1,6-hexanediol residues and having an inherent viscosity of 0.32 and a hydroxyl number of 13.

III. Polyester of diacid residues consisting of 100 mole percent terephthalic acid residues and diol residues consisting of 15 mole percent 2,2-dimethyl-1,3-propanediol and 85 mole percent 1,6-hexanediol residues and having an inherent viscosity of 0.32 and a hydroxyl number of 17.

IV. Polyester of diacid residues consisting of 100 mole percent terephthalic acid residues and diol residues consisting of 25 mole percent 2,2-dimethyl-1,3-propanediol and 75 mole percent 1,10-decanediol residues and having an inherent viscosity of 0.28 and a hydroxyl number of 21.

V. Polyester of diacid residues consisting of 95 mole percent terephthalic acid and 5 mole percent trans-1,4-cyclohexanedicarboxylic acid residues and diol residues consisting of 100 mole percent 1,6-hexanediol residues and having an inherent viscosity of 0.21-0.22 and a hydroxyl number of 45-55.

In Comparative Examples 4 and 7 the cross-linking agent employed was Hüls 1530, a mixture consisting primarily of the ε-caprolactam-blocked, difunctional, monomeric isophorone diisocyanate and the ε-caprolactam-blocked, trifunction trimer of isophorone diisocyanate. Hüls 1530 is commonly used in commercially-available powder coating compositions.

The inherent viscosities (I.V.; dl/g) referred to herein were measured at 25° C. using 0.5 g polymer per 100 mL of a solvent consisting of 60 parts by weight phenol and 40 parts by weight tetrachloroethane. Acid and hydroxyl numbers were determined by titration and are reported herein as mg of KOH consumed for each gram of polymer. The glass transition temperatures (Tg) were determined by differential scanning calorimetry (DSC) on the second heating cycle at a scanning rate of 20° C. per minute after the sample has been heated to melt and quenched to below the Tg of the polymer. Tg values are reported as the midpoint of the transition and Tm at peaks of transitions.

Coatings were prepared on 3 inch by 9 inch panels of 24-gauge, polished, cold roll steel, the surface of which has been zinc phosphated (Bonderite 37, The Parker Company). The powder coating compositions were applied electrostatically to one side of the panels and the coatings were cured (cross-linked) by heating the coated panels in an oven at varying temperatures and for a specified period of time.

Impact strengths were determined using an impact tester (Gardner Laboratory, Inc.) according to ASTM D2794.84. A weight with a ⅝-inch diameter, hemispherical nose was dropped within a slide tube from a specified height to drive into the front (coated face) or back of the panel. The highest impact which did not crack the coating was recorded in inch-pounds, front and reverse (back).

The pencil hardness of the coatings was determined according to ASTM 3363-74 (reapproved 1980) and is reported as the hardest lead which does not cut into the coating. The results of the pencil hardness test are expressed according to the following scale: (softest) 6B, 5B, 4B, 3B, 2B, B, HB, F, H, 2H, 3H, 4H, 5H, 6H (hardest). The conical mandrel test is conducted according to ASTM 522-85 by bending a panel over a 15 second period using a 0.125 inch conical mandrel (Gardner Laboratory, Inc.). A pass or fail is recorded.

The degree to which the coatings are cured is indicated by the methyl ethyl ketone (MEK) double rub test wherein a coated panel was rubbed with a MEK-soaked, 16 layer-thick square of cheesecloth attached to the rounded end of a 2 pound ball peen hammer. Each forward-backward stroke (double rub) was counted as one stroke and the result of each test was reported as the number of strokes required to remove the coating and expose the bare metal panel. Usually, a coating was exposed to a maximum of 200 double rubs and if the coating withstood the 200 double rubs, the result of the test was reported as >200. If the exact number of rubs required to remove the coating is uncertain, the result of the MEK double rub test is reported as less than the total number of strokes used in the test, e.g. 50. While the exact number of rubs required to remove a coating may be uncertain for some tests, the fact that the formulation was not completely cured can be ascertained.

The flexibility of the coatings was determined in accordance with ASTM 4145-83 at ambient or room temperature (T.Bend R.T. Flex.) by bending or folding a coated panel back against itself, using a hydraulic jack pressurized to 20,000 pounds per square inch (psi), until the apex of the bend is as flat as can be reasonably achieved. This initial bend is referred to as 0T meaning that there is nothing (zero thicknesses) between the bent portions of the panel. The bend is examined using a 10X magnifying glass and a pass or fail is recorded depending on whether fractures of the coating are observed. In some cases coated panels which had passed the 0T bend were subjected to a more strenuous test which involved heating the bent panel at 200° F. for 20 minutes and then inspecting the bend for fractures as described above.

Table I sets forth the thickness (mils) of the coatings and the temperatures and time periods (° F./minutes) employed in curing the coatings. Table I also sets forth the properties of the coatings determined as described hereinabove.

EXAMPLE 4

| | |
|---|---|
| 162.0 g | Semi-crystalline polyester II. |
| 162.0 g | Amorphous polyester - Cargill 3000. |
| 76.0 g | Blocked polyisocyanate of Example 1. |
| 4.0 g | Dibutyltin dilaurate. |
| 4.0 g | Benzoin. |
| 4.8 g | Modaflow flow aid, and |

EXAMPLE 5

| | |
|---|---|
| 238.7 g | Semi-crystalline polyester II, |
| 102.3 g | Amorphous polyester - Cargill 3000, |
| 59.0 g | Blocked polyisocyanate of Example 1, |
| 4.0 g | Dibutyltin dilaurate, |
| 4.0 g | Benzoin, |
| 4.8 g | Modaflow flow aid, and |
| 200.0 g | Titanium dioxide pigment. |

EXAMPLE 6

| | |
|---|---|
| 328.9 g | Semi-crystalline polyester I, |
| 71.1 g | Blocked polyisocyanate of Example 1, |
| 4.0 g | Dibutyltin dilaurate, |
| 4.0 g | Benzoin, |
| 4.8 g | Modaflow flow aid, and |
| 200.0 g | Titanium dioxide pigment. |

EXAMPLE 7

| | |
|---|---|
| 358.8 g | Semi-crystalline polyester III, |
| 41.2 g | Blocked polyisocyanate of Example 1, |
| 4.0 g | Dibutyltin dilaurate, |
| 4.0 g | Benzoin, |
| 4.8 g | Modaflow flow aid, and |
| 200.0 g | Titanium dioxide pigment. |

COMPARATIVE EXAMPLE 1

| | |
|---|---|
| 93.6 g | Semi-crystalline polyester II, |
| 218.4 g | Amorphous polyester - Cargill 3000, |
| 88.0 g | Blocked polyisocyanate of Example 1, |
| 4.0 g | Dibutyltin dilaurate, |
| 4.0 g | Benzoin, |
| 4.8 g | Modaflow flow aid, and |
| 200.0 g | Titanium dioxide pigment. |

COMPARATIVE EXAMPLE 2

| | |
|---|---|
| 294.0 g | Amorphous polyester - Cargill 3000, |
| 106.0 g | Blocked polyisocyanate of Example 1, |
| 4.0 g | Dibutyltin dilaurate, |
| 4.0 g | Benzoin, |
| 4.8 g | Modaflow flow aid, and |
| 200.0 g | Titanium dioxide pigment. |

COMPARATIVE EXAMPLE 3

| | |
|---|---|
| 316.0 g | Amorphous polyester - Cargill 3016, |
| 84.0 g | Blocked polyisocyanate of Example 1, |
| 4.0 g | Dibutyltin dilaurate, |
| 4.0 g | Benzoin, |
| 4.8 g | Modaflow flow aid, and |
| 200.0 g | Titanium dioxide pigment. |

COMPARATIVE EXAMPLE 4

| | |
|---|---|
| 353.4 g | Semi-crystalline polyester I, |
| 46.6 g | Huls 1530 ε-caprolactam-blocked polyisocyanate, |
| 4.0 g | Dibutyltin dilaurate, |
| 4.0 g | Benzoin, |
| 4.8 g | Modaflow flow aid, and |
| 200.0 g | Titanium dioxide pigment. |

EXAMPLE 8

| | |
|---|---|
| 328.9 g | Semi-crystalline polyester I, |
| 71.1 g | Blocked polyisocyanate of Example 1, |
| 4.0 g | Dimethyltin dichloride, |
| 4.0 g | Benzoin, |
| 4.8 g | Modaflow flow aid, and |
| 200.0 g | Titanium dioxide pigment. |

EXAMPLE 9

| | |
|---|---|
| 328.9 g | Semi-crystalline polyester I, |
| 71.1 g | Blocked polyisocyanate of Example 1, |
| 4.0 g | Dibutyltin dilaurate, |
| 0.7 g | 1,4-Diazabicyclo[2.2.2]octane, |
| 4.0 g | Benzoin, |
| 4.8 g | Modaflow flow aid, and |
| 200.0 g | Titanium dioxide pigment. |

EXAMPLE 10

| | |
|---|---|
| 350.3 g | Semi-crystalline polyester IV, |
| 49.7 g | Blocked polyisocyanate of Example 1, |
| 4.0 g | Dibutyltin dilaurate, |
| 4.0 g | Benzoin, |
| 4.8 g | Modaflow flow aid, and |
| 200.0 g | Titanium dioxide pigment. |

EXAMPLE 11

| | |
|---|---|
| 239.4 g | Semi-crystalline polyester IV, |
| 102.6 g | Amorphous polyester - Rucote 107, |
| 58.0 g | Blocked polyisocyanate of Example 1, |
| 4.0 g | Dibutyltin dilaurate, |
| 4.0 g | Benzoin, |
| 4.8 g | Modaflow flow aid, and |
| 200.0 g | Titanium dioxide pigment. |

EXAMPLE 12

| | |
|---|---|
| 167.4 g | Semi-crystalline polyester IV, |
| 167.4 g | Amorphous polyester - Rucote 107, |
| 65.2 g | Blocked polyisocyanate of Example 1, |
| 4.0 g | Dibutyltin dilaurate, |
| 4.0 g | Benzoin, |
| 4.8 g | Modaflow flow aid, and |
| 200.0 g | Titanium dioxide pigment. |

COMPARATIVE EXAMPLE 5

| | |
|---|---|
| 97.6 g | Semi-crystalline polyester IV, |
| 227.9 g | Amorphous polyester - Rucote 107, |
| 74.6 g | Blocked polyisocyanate of Example 1, |
| 4.0 g | Dibutyltin dilaurate, |
| 4.0 g | Benzoin, |
| 4.8 g | Modaflow flow aid, and |

EXAMPLE 13

| | |
|---|---|
| 367.9 g | Semi-crystalline polyester III, |
| 32.1 g | Blocked polyisocyanate of Example 3, |
| 4.0 g | Dibutyltin dilaurate, |
| 4.0 g | Benzoin, |
| 4.8 g | Modaflow flow aid, and |
| 200.0 g | Titanium dioxide pigment. |

EXAMPLE 14

| | |
|---|---|
| 238.8 g | Semi-crystalline polyester III, |
| 102.3 g | Amorphous polyester - AZS 50, |
| 58.9 g | Blocked polyisocyanate of Example 3, |
| 4.0 g | Dibutyltin dilaurate, |
| 4.0 g | Benzoin, |
| 4.8 g | Modaflow flow aid, and |
| 200.0 g | Titanium dioxide pigment. |

COMPARATIVE EXAMPLE 6

| | |
|---|---|
| 308.2 g | Amorphous polyester - AZS 50, |
| 91.8 g | Blocked polyisocyanate of Example 3, |
| 4.0 g | Dibutyltin dilaurate, |
| 4.0 g | Benzoin, |
| 4.8 g | Modaflow flow aid, and |
| 200.0 g | Titanium dioxide pigment. |

EXAMPLE 15

| | |
|---|---|
| 1483.0 g | Semi-crystalline polyester II, |
| 260.0 g | Blocked polyisocyanate of Example 2, |
| 17.5 g | Dibutyltin dilaurate, |
| 17.4 g | Benzoin, |
| 20.9 g | Modaflow flow aid, and |
| 1200.0 g | Titanium dioxide pigment. |

EXAMPLE 16

| | |
|---|---|
| 964.0 g | Semi-crystalline polyester II, |
| 413.0 g | Amorphous polyester - Rucote 107, |
| 368.0 g | Blocked polyisocyanate of Example 2, |
| 17.5 g | Dibutyltin dilaurate, |
| 17.4 g | Benzoin, |
| 20.9 g | Modaflow flow aid, and |
| 1200.0 g | Titanium dioxide pigment. |

COMPARATIVE EXAMPLE 7

| | |
|---|---|
| 1531.0 g | Amorphous polyester - Rucote 107, |
| 214.0 g | Huls 1530 ε-caprolactam-blocked polyisocyanate, |
| 17.5 g | Dibutyltin dilaurate, |
| 17.4 g | Benzoin, |
| 20.9 g | Modaflow flow aid, and |
| 1200.0 g | Titanium dioxide pigment. |

EXAMPLE 17

| | |
|---|---|
| 1467.0 g | Semi-crystalline polyester II, |
| 277.0 g | Blocked polyisocyanate of Example 1, |
| 17.5 g | Dibutyltin dilaurate, |
| 17.4 g | Benzoin, |
| 20.9 g | Modaflow flow aid, and |
| 1200.0 g | Titanium dioxide pigment. |

EXAMPLE 18

| | |
|---|---|
| 948.0 g | Semi-crystalline polyester I, |
| 406.0 g | Amorphous polyester - Rucote 107, |
| 390.0 g | Blocked polyisocyanate of Example 1, |
| 17.5 g | Dibutyltin dilaurate, |
| 17.4 g | Benzoin, |
| 20.9 g | Modaflow flow aid, and |
| 1200.0 g | Titanium dioxide pigment. |

EXAMPLE 19

| | |
|---|---|
| 314.9 g | Semi-crystalline polyester V, |
| 85.1 g | Blocked polyisocyanate of Example 1, |
| 4.0 g | Dibutyltin dilaurate, |
| 4.0 g | Benzoin, |
| 4.8 g | Modaflow flow aid, and |
| 200.0 g | Titanium dioxide pigment. |

EXAMPLE 20

| | |
|---|---|
| 218.7 g | Semi-crystalline polyester V, |
| 93.7 g | Amorphous polyester - Rucote 107, |
| 87.6 g | Blocked polyisocyanate of Example 1, |
| 4.0 g | Dibutyltin dilaurate, |
| 4.0 g | Benzoin, |
| 4.8 g | Modaflow flow aid, and |
| 200.0 g | Titanium dioxide pigment. |

EXAMPLE 21

| | |
|---|---|
| 155.4 g | Semi-crystalline polyester V, |
| 155.4 g | Amorphous polyester - Rucote 107, |
| 89.2 g | Blocked polyisocyanate of Example 1, |
| 4.0 g | Dibutyltin dilaurate, |
| 4.0 g | Benzoin, |
| 4.8 g | Modaflow flow aid, and |
| 200.0 g | Titanium dioxide pigment. |

COMPARATIVE EXAMPLE 8

| | |
|---|---|
| 92.7 g | Semi-crystalline polyester V, |
| 216.4 g | Amorphous polyester - Rucote 107, |
| 90.9 g | Blocked polyisocyanate of Example 1, |
| 4.0 g | Dibutyltin dilaurate, |
| 4.0 g | Benzoin, |
| 4.8 g | Modaflow flow aid, and |
| 200.0 g | Titanium dioxide pigment. |

TABLE I

| Example | Cure Conditions | Thick. | Impact Strength Front | Impact Strength Reverse | Pencil Hardness | Conical Mandrel | T-Bend R.T. Flex. | T-Bend 200° Flex. | MEK Rub |
|---|---|---|---|---|---|---|---|---|---|
| 4 | 350/25 | 2.0 | <20 | <20 | F | Fail | — | — | >200 |
| 4 | 350/10 | 1.8 | 40 | <20 | F | Fail | — | — | >200 |
| 4 | 330/25 | 2.1 | 20 | <20 | HB | Pass | — | — | >200 |
| 4 | 300/35 | 2.1 | <20 | <20 | HB | Fail | — | — | >155 |
| 5 | 350/25 | 2.0 | 20 | <20 | HB | Pass | Fail | — | >200 |
| 5 | 350/10 | 2.0 | 20 | <20 | F | Pass | Fail | — | >200 |
| 5 | 330/25 | 1.9 | 60 | 60 | HB | Pass | Marg. | — | >200 |
| 5 | 300/35 | 1.7 | 40 | 20 | F | Pass | Fail | — | >200 |
| 6 | 350/25 | 1.9 | 160 | 160 | HB | Pass | Pass | — | >200 |
| 6 | 330/10 | 1.9 | 160 | 160 | 2B | Pass | Pass | — | >200 |
| 6 | 350/25 | 2.0 | 160 | 160 | 2B | Pass | Pass | — | >200 |
| 6 | 300/35 | 1.6 | 160 | 160 | HB | Pass | Pass | — | >200 |
| 6 | 275/25 | 2.0 | >160 | >160 | 4B | Pass | Pass | — | >200 |
| 7 | 350/25 | 2.3 | 160 | 160 | 3B | Pass | Pass | — | >200 |
| 7 | 350/10 | 2.3 | 160 | 160 | B | Pass | Pass | — | >200 |
| 7 | 330/25 | 2.5 | 160 | 160 | 4B | Pass | Pass | — | >200 |
| 7 | 300/35 | 2.5 | 160 | 160 | 5B | Pass | Pass | — | >200 |
| 7 | 275/35 | 2.2 | 160 | 160 | 5B | Pass | Pass | — | >200 |
| 7 | 275/25 | 2.3 | 160 | 160 | 5B | Pass | Pass | — | >200 |
| C-1 | 350/25 | 1.8 | <20 | 20 | HB | Pass | — | — | <160 |
| C-1 | 350/10 | 1.8 | <20 | 20 | F | Pass | — | — | <100 |
| C-1 | 330/35 | 1.5 | 100 | 100 | HB | Pass | — | — | <130 |
| C-1 | 300/35 | 1.9 | <20 | <20 | HB | Fail | — | — | <60 |
| C-2 | 350/25 | 2.1 | <20 | <20 | 3H | Fail | — | — | >200 |
| C-2 | 350/10 | 2.3 | <20 | <20 | — | Fail | — | — | 140 |
| C-2 | 330/25 | 2.1 | <20 | <20 | 3H | Fail | — | — | 195 |
| C-2 | 300/25 | 2.1 | <20 | <20 | H | Fail | — | — | <79 |
| C-3 | 350/25 | 2.2 | <20 | <20 | 2H | Fail | — | — | 190 |
| C-3 | 350/10 | 2.1 | <20 | <20 | 2H | Pass | — | — | 120 |
| C-3 | 330/25 | 2.2 | <20 | <20 | 2H | Fail | — | — | 195 |
| C-3 | 300/25 | 1.9 | 80 | <20 | H | Fail | — | — | 10 |
| C-3 | 300/35 | 2.0 | 20 | <20 | 2H | Fail | — | — | 35 |
| C-4 | 350/25 | 2.0 | 160 | 160 | 3B | Pass | Pass | — | >200 |
| C-4 | 330/25 | 1.7 | 160 | 160 | 3B | Pass | Pass | — | <120 |
| C-4 | 300/35 | 1.9 | 20 | <20 | 3B | Pass | Fail | — | <20 |
| 8 | 275/35 | 1.7 | 160 | 160 | HB | Pass | Pass | — | >200 |
| 8 | 275/25 | 2.0 | 160 | 160 | HB | Pass | Pass | — | >200 |
| 8 | 260/25 | 2.0 | 20 | <20 | HB | Pass | Fail | — | >200 |
| 8 | 260/35 | 2.1 | 160 | 160 | HB | Pass | Fail | — | >200 |
| 9 | 275/25 | 1.9 | 160 | 120 | B | Pass | Pass | — | >200 |
| 9 | 260/25 | 2.1 | 20 | <20 | HB | Pass | Pass | — | >200 |
| 9 | 260/35 | 2.1 | 160 | 160 | F | Pass | Fail | — | >200 |
| 10 | 350/25 | 2.0 | 160 | 160 | B | Pass | Pass | Pass | >200 |
| 10 | 300/25 | 2.2 | 160 | 160 | HB | Pass | Pass | Pass | >200 |
| 10 | 275/25 | 2.4 | 160 | 160 | HB | Pass | Pass | Fail | >200 |
| 11 | 350/25 | 2.0 | 160 | 100 | 3B | Pass | Fail | — | >200 |
| 11 | 300/25 | 2.0 | 160 | 100 | B | Pass | Fail | — | >200 |
| 11 | 275/25 | 1.9 | 140 | 100 | B | Pass | Fail | — | >200 |
| 12 | 350/25 | 1.9 | 160 | 160 | 2B | Pass | Fail | — | >200 |
| 12 | 300/25 | 2.2 | 160 | 160 | B | Pass | Fail | — | >200 |
| 12 | 275/25 | 1.9 | <20 | 20 | 4B | Pass | Fail | — | <20 |
| C-5 | 350/25 | 2.0 | 20 | <20 | B | Pass | Fail | — | >200 |
| C-5 | 300/25 | 2.3 | <20 | <20 | 2B | Fail | Fail | — | <100 |
| C-5 | 275/25 | 2.1 | <20 | <20 | 2B | Fail | Fail | — | <8 |
| 13 | 350/25 | — | 160 | 160 | 2H | Pass | — | — | >200 |
| 13 | 330/25 | — | 160 | 120 | 2H | Pass | — | — | >200 |
| 13 | 300/25 | — | 160 | 160 | H | Pass | — | — | >200 |
| 13 | 275/25 | — | <20 | <20 | — | Pass | — | — | <50 |
| 14 | 350/25 | — | 120 | 160 | HB | Pass | — | — | 120 |
| 14 | 330/25 | — | 160 | 160 | HB | Pass | — | — | 100 |
| 14 | 300/25 | — | 160 | <60 | B | Pass | — | — | 70 |
| C-6 | 350/25 | — | 160 | 160 | HB | Pass | — | — | >200 |
| C-6 | 330/25 | — | 160 | 160 | 5H | Pass | — | — | 165 |
| C-6 | 300/25 | — | <60 | <60 | — | Fail | — | — | <50 |
| 15 | 300/25 | 3.1-3.4 | 160 | 160 | HB | — | — | — | >100 |
| 15 | 275/25 | 2.4-3.0 | 160 | 160 | HB | — | — | — | >100 |
| 16 | 300/25 | 2.0 | 160 | 60 | HB | — | — | — | >100 |
| 16 | 275/25 | 1.9-2.7 | 20 | <20 | HB | — | — | — | <25 |
| C-7 | 300/25 | 2.3-3.0 | 20 | <20 | — | — | — | — | Fail |
| C-7 | 275/25 | 2.7-3.3 | <20 | <20 | — | — | — | — | Fail |
| 17 | 300/25 | 1.9-2.4 | 160 | 160 | 3B | — | — | — | >100 |
| 17 | 275/25 | 2.2-2.3 | 160 | 160 | 3B | — | — | — | >100 |
| 17 | 275/35 | 2.4-2.8 | 160 | 160 | HB | — | — | — | >100 |
| 18 | 300/25 | 1.5-2.2 | 160 | 160 | H | — | — | — | >100 |
| 18 | 275/25 | 2.3-2.8 | 20 | <20 | B | — | — | — | <25 |
| 19 | 350/25 | 2.0 | 160 | 160 | B | Pass | Pass | Pass | >200 |
| 19 | 330/25 | 1.7 | 160 | 160 | B | Pass | Pass | Pass | >200 |
| 19 | 300/25 | 2.0 | 160 | 160 | 3B | Pass | Pass | Pass | >200 |
| 19 | 275/25 | — | 160 | 160 | B | — | Pass | Pass | >200 |

TABLE I-continued

| Example | Cure Conditions | Thick. | Impact Strength | | Pencil Hardness | Conical Mandrel | T-Bend R.T. Flex. | T-Bend 200° Flex. | MEK Rub |
| --- | --- | --- | --- | --- | --- | --- | --- | --- | --- |
| | | | Front | Reverse | | | | | |
| 20 | 350/25 | 1.8 | 160 | 160 | B | Pass | Pass | Pass | >200 |
| 20 | 330/25 | 2.0 | 160 | 160 | B | Pass | Pass | Pass | >200 |
| 20 | 300/25 | 1.9 | 160 | 160 | B | Pass | Pass | Pass | >200 |
| 20 | 275/25 | — | 160 | 160 | B | — | Pass | Pass | >200 |
| 21 | 350/25 | 2.0 | 140 | 20 | H | Pass | Fail | — | >200 |
| 21 | 330/25 | 2.1 | 160 | 20 | H | Pass | Fail | — | >200 |
| 21 | 300/25 | 1.8 | 160 | 20 | F | Pass | Fail | — | >200 |
| 21 | 275/25 | — | <20 | 20 | — | — | Fail | — | <20 |
| C-8 | 350/25 | 2.0 | 20 | 20 | H | Pass | Fail | — | >200 |
| C-8 | 330/25 | 1.9 | 40 | 20 | H | Pass | Fail | — | >200 |
| C-8 | 300/25 | 2.0 | 20 | 20 | H | Pass | Fail | — | <150 |

The following examples describe typical procedures for the preparation of the semi-crystalline polyesters employed herein.

REFERENCE EXAMPLE 1

To a 5-L, 3 necked, round-bottom flask were charged terephthalic acid (1300.6 g, 7.83 mol), 2,2-dimethyl-1,3-propanediol (132.1 g, 1.23 mol), 1,6-hexanediol (849.1 g, 7.19 mol) and dibutyltin oxide (2.3 g mol). The flask was purged with nitrogen and heated to 190° C. over 90 minutes. The reaction mixture was maintained at 190° C. until 15 to 20 percent of the theoretical condensate was evolved and then the temperature was increased to and maintained at 230° C. until the acid number of the polymer was below 10. The molten polymer was poured into a syrup can and allowed to solidify. The polyester had a hydroxyl number of 13, an acid number of 8, an inherent viscosity of 0.31 and a glass transition temperature of 10.0° C.

REFERENCE EXAMPLE 2

Using the procedure described in Reference Example 1, terephthalic acid (1114.8 g, 6.71 mol), 2,2-dimethyl-1,3-propanediol (187.4 g, 1.8 mol), 1,10-decanediol (939.4 g, 5.4 mol) and dibutyltin oxide (2.3 g) were reacted and polymerized. The semi-crystalline polyester obtained had an acid number of 5, an inherent viscosity of 0.25 and a glass transition temperature of 3° C.

REFERENCE EXAMPLE 3

Terephthalic acid (253.87 g, 1.523 mol), 1,4-cyclohexanedicarboxylic acid (cis:trans=about 60:40, 48.4 g, 0.27 mol), and butanestannoic acid (FASCAT 4100, 0.6 g) were added to a melt of 1,10-decanediol (369.9 g, 2.13 mol) in a 5 L, 3-necked, round-bottom flask. The contents of the flask were swept with 1.0 standard cubic feet per hour (scfh) nitrogen and heated to 200° C. over a period of about 30 minutes. The reaction mixture was heated at 200° C. for 3 hours, at 210° C. for 2 hours and at 220° C. for 1 hour. The temperature then was raised to and maintained at 230° C. until the acid number of the polyester was less than 10. The molten polymer was poured into a syrup can where it was allowed to cool to a white solid. The polyester thus obtained had an I.V. of 0.222, a hydroxyl number of 43.0 and an acid number of 0.2. Differential scanning calorimetry showed a melting point at 116° C. and a heat of fusion of 15.1 cal/g.

The invention has been described in detail with particular reference to preferred embodiments thereof, but it will be understood that variations and modifications can be effected within the spirit and scope of the invention.

We claim:

1. A polyester composition comprising:
   (1) a semi-crystalline polyester having a glass transition temperature of not more than 50° C., a number average molecular weight of about 500 to 10,000, a hydroxyl number of about 5 to 200 and an inherent viscosity of about 0.1 to 0.5 and comprised of:
      (a) diacid residues comprised of at least 80 mole percent of terephthalic acid residues, 1,4-cyclohexanedicarboxylic acid residues, 1,3-cyclohexanedicarboxylic acid residues or a mixture thereof; and
      (b) diol residues comprised of (i) about 50 to 100 mole percent of residues having the formula —O(CH$_2$)$_n$O— wherein n is about 6 to 12 and (ii) about 0 to 50 mole percent of 2,2-dimethyl-1,3-propanediol residues, provided that at least 90 mole percent of the diol residues are residues having the formula —O(CH$_2$)$_n$O— and 2,2-dimethyl-1,3-propanediol residues; and
   (2) a cross-linking effective amount of at least one oxime-blocked polyisocyanate which is the reaction product of an oxime selected from 2,4-dimethyl3-pentanone oxime and 2,6-dimethyl-4-heptanone oxime and a polyisocyanate selected from the trimer of isophorone diisocyanate, methylene-bis(4,4'-cyclohexylisocyanate), 1,3-bis(1-isocyanato-1-methylethyl)benzene and 1,4-bis(1-isocyanato-1-methylethyl)benzene.

2. A polyester composition according to claim 1 comprising:
   (1) a semi-crystalline polyester having a glass transition temperature of less than 20° C., a melting point of about 90° to 140° C., a hydroxyl number of about 8 to 60 and an inherent viscosity of about 0.1 to 0.4 comprised of:
      (a) diacid residues consisting essentially of about 50 to 100 mole percent terephthalic acid residues and 0 to about 50 mole percent 1,4-cyclohexanedicarboxylic acid residues, 1,3-cyclohexanedicarboxylic acid residues or a mixture thereof; and
      (b) diol residues consisting essentially of about 70 to 100 mole percent of residues having the formula —O(CH$_2$)$_n$O— wherein n is about 6 to 12 and about 0 to 30 mole percent 2,2-dimethyl-1,3-propanediol residues, and
   (2) about 8 to 25 weight percent, based on the weight of (1) and (2), of an oxime-blocked polyisocyanate compound which is the reaction product of an oxime selected from 2,4-dimethyl-3-pentanone oxime and 2,6-dimethyl-4-heptanone oxime and the trimer of isophorone diisocyanate.

3. A polyester composition according to claim 2 wherein the oxime-blocked polyisocyanate is the triisocyanato, isocyanurate trimer of 3-isocyanato.methyl-3,5,5-trimethylcyclohexylisocyanate, the three isocyanato groups of which have been converted to groups having the formula

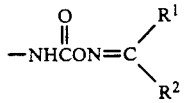

wherein $R_1$ and $R_2$ each is isopropyl or isobutyl.

4. A polyester composition according to claim 1 comprising:
(1) a semi-crystalline polyester having a glass transition temperature of less than 20° C., a melting point of about 90° to 140° C., a hydroxyl number of about 8 to 60 and an inherent viscosity of about 0.1 to 0.4 comprised of:
   (a) diacid residues consisting essentially of about 50 to 100 mole percent terephthalic acid residues and 0 to about 50 mole percent 1,4-cyclohexanedicarboxylic acid residues, 1,3-cyclohexanedicarboxylic acid residues or a mixture thereof; and
   (b) diol residues consisting essentially of about 70 to 100 mole percent of residues having the formula —O(CH$_2$)$_n$O— wherein n is about 6 to 12 and about 0 to 30 mole percent 2,2-dimethyl-1,3-propanediol residues, and
(2) about 8 to 25 weight percent, based on the weight of (1) and (2), of an oxime-blocked polyisocyanate compound having the formula:

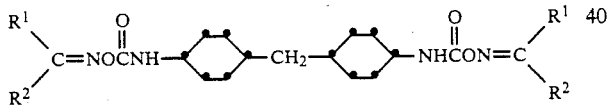

wherein $R^1$ and $R^2$ each is isopropyl or isobutyl.

5. A polyester composition according to claim 1 comprising:
(1) a semi-crystalline polyester having a glass transition temperature of less than 20° C., a melting point of about 90° to 140° C., a hydroxyl, number of about 8 to 60 and an inherent viscosity of about 0.1 to 0.4 comprised of:
   (a) diacid residues consisting essentially of about 50 to 100 mole percent terephthalic acid residues and 0 to about 50 mole percent 1,4-cyclohexanedicarboxylic acid residues, 1,3-cyclohexanedicarboxylic acid residues or a mixture thereof; and
   (b) diol residues consisting essentially of about 70 to 100 mole percent of residues having the formula —O(CH$_2$)$_n$O— wherein n is about 6 to 12 and about 0 to 30 mole percent 2,2-dimethyl-1,3-propanediol residues, and
(2) about 8 to 25 weight percent, based on the weight of (1) and (2), of an oxime-blocked polyisocyanate compound having the formula:

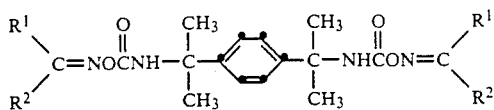

wherein $R^1$ and $R^2$ each is isopropyl or isobutyl.

6. A polyester composition according to claim 1 comprising:
(1) a semi-crystalline polyester having a glass transition temperature of less than 20° C., a melting point of about 90° to 140° C., a hydroxyl number of about 8 to 60 and an inherent viscosity of about 0.1 to 0.4 comprised of:
   (a) diacid residues consisting essentially of about 50 to 100 mole percent terephthalic acid residues and 0 to about 50 mole percent 1,4-cyclohexanedicarboxylic acid residues, 1,3-cyclohexanedicarboxylic acid residues or a mixture thereof; and
   (b) diol residues consisting essentially of about 70 to 100 mole percent of residues having the formula —O(CH$_2$)$_n$O— wherein n is about 6 to 12 and about 0 to 30 mole percent 2,2-dimethyl-1,3-propanediol residues, and
(2) about 8 to 25 weight percent, based on the weight of (1) and (2), of an oxime-blocked polyisocyanate compound having the formula:

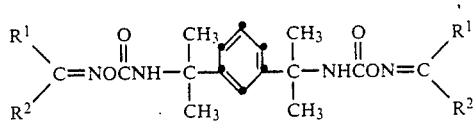

wherein $R^1$ and $R^2$ each is isopropyl or isobutyl.

7. A polyester composition comprising:
(1) about 50 to 90 weight percent, based on the weight of (1) and (2), of a semi-crystalline polyester having a glass transition temperature of not more than 56° C., a number average molecular weight of about 500 to 10,000, a hydroxyl number of about 5 to 200 and an inherent viscosity of about 0.1 to 0.5 and comprised of:
   (a) diacid residues comprised of at least 80 mole percent of terephthalic acid residues, 1,4-cyclohexanedicarboxylic acid residues, 1,3-cyclohexanedicarboxylic acid residues or a mixture thereof; and
   (b) diol residues comprised of (i) about 50 to 100 mole percent of residues having the formula —O(CH$_2$)$_n$O— wherein n is about 6 to 12 and (ii) about 0 to 50 mole percent of 2,2-dimethyl-1,3-propanediol residues, provided that at least 90 mole percent of the diol residues are residues having the formula —O(CH$_2$)$_n$O— and 2,2-dimethyl-1,3-propanediol residues;
(2) about 50 to 10 weight percent, based on the weight of (1) and (2), of one or more amorphous polyesters having a glass transition temperature of greater than 40° C., a hydroxyl number of about 20 to 200 and an inherent viscosity of about 0.1 to 0.5; and
(3) a cross-linking effective amount of at least one oxime-blocked polyisocyanate which is the reaction product of an oxime selected from 2,4-dimethyl-3-pentanone oxime and 2,6-dimethyl-4-heptanone oxime and a polyisocyanate selected from the trimer of isophorone diisocyanate, methylenebis(4,4'-cyclohexylisocyanate), 1,3-bis(1-isocyanato-1-methylethyl)benzene and 1,4-bis(1-isocyanato-1-methylethyl)benzene.

8. A polyester composition according to claim 7 comprising:
(1) about 50 to 90 weight percent, based on the weight of (1) and (2), of a semi-crystalline polyester having a glass transition temperature of less than 20° C., a melting point of about 90° to 140° C., a hydroxyl number of about 8 to 60 and an inherent viscosity of about 0.1 to 0.4 comprised of:
(a) diacid residues consisting essentially of about 50 to 100 mole percent terephthalic acid residues and 0 to about 50 mole percent 1,4-cyclohexanedicarboxylic acid residues, 1,3-cyclohexanedicarboxylic acid residues or a mixture thereof; and
(b) diol residues consisting essentially of about 70 to 100 mole percent of residues having the formula —O(CH$_2$)$_n$O— wherein n is about 6 to 12 and about 0 to 30 mole percent 2,2-dimethyl 1,3-propanediol residues;
(2) about 50 to 10 weight percent, based on the weight of (1) and (2), of one or more amorphous polyesters having a glass transition temperature of greater than 55° C., a hydroxyl number of about 25 to 80, an acid number of not more than 15 and an inherent viscosity of about 0.10 to 0.4 comprised of:
(a) diacid residues of which at least 50 mole percent are terephthalic acid residues;
(b) diol residues of which at least 50 mole percent are 2,2-dimethyl-1,3-propanediol residues; and
(c) up to 15 mole percent, based on the total moles of (b) and (c), of trimethylolpropane residues; and
(3) about 8 to 25 weight percent, based on the weight of (1), (2) and (3), of an oxime-blocked polyisocyanate compound which is the reaction product of an oxime selected from 2,4-dimethyl-3-pentanone oxime and 2,6-dimethyl-4-heptanone and the trimer of isophorone diisocyanate.

9. A polyester composition according to claim 8 wherein the amorphous polyester has a glass transition temperature (Tg) of about 55° to 65° C., a hydroxyl number of about 35 to 65, an acid number of not more than 10 and an inherent viscosity of about 0.10 to 0.25 and consisting essentially of terephthalic acid residues, 2,2-dimethyl-1,3-propanediol residues and up to 15 mole percent, based on the total moles of trimethylolpropane and 2,2-dimethyl-1,3-propanediol residues, of trimethylolpropane residues.

10. A polyester composition according to claim 17 comprising:
(1) about 50 to 90 weight percent, based on the weight of (1) and (2), of a semi-crystalline polyester having a glass transition temperature of less than 20° C., a melting point of about 90° to 140° C., a hydroxyl number of about 8 to 60 and an inherent viscosity of about 0.1 to 0.4 comprised of:
(a) diacid residues consisting essentially of about 50 to 100 mole percent terephthalic acid residues and 0 to about 50 mole percent 1,4-cyclohexanedicarboxylic acid residues, 1,3-cyclohexanedicarboxylic acid residues or a mixture thereof; and
(b) diol residues consisting essentially of about 70 to 100 mole percent of residues having the formula —O(CH$_2$)$_n$O— wherein n is about 6 to 12 and about 0 to 30 mole percent 2,2-dimethyl-1,3-propanediol residues;
(2) about 50 to 10 weight percent, based on the weight of (1) and (2), of one or more amorphous polyesters having a glass transition temperature of greater than 55° C., a hydroxyl number of about 25 to 80, an acid number of not more than 15 and an inherent viscosity of about 0.10 to 0.4 comprised of:
(a) diacid residues of which at least 50 mole percent are terephthalic acid residues;
(b) diol residues of which at least 50 mole percent are 2,2-dimethyl-1,3-propanediol
(c) up to 15 mole percent, based on the total moles of (b) and (c), of trimethylolpropane residues; and
(3) about 8 to 25 weight percent, based on the weight of (1), (2) and (3), of an oxime-blocked polyisocyanate compound having the formula:

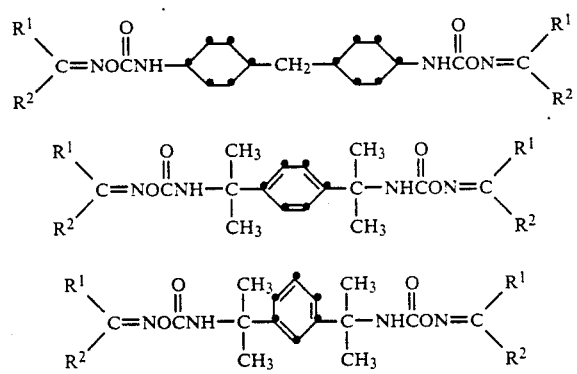

wherein R$^1$ and R$^2$ each is isopropyl or isobutyl.

11. A polyester composition according to claim 10 wherein the amorphous polyester has a glass transition temperature (Tg) of about 55° to 65° C., a hydroxyl number of about 35 to 65, an acid number of not more than 10 and an inherent viscosity of about 0.10 to 0.25 and consisting essentially of terephthalic acid residues, 2,2-dimethyl-1,3-propanediol residues and up to 15 mole percent, based on the total moles of trimethylolpropane and 2,2-dimethyl-1,3-propanediol residues, of trimethylolpropane residues.

12. A thermosetting coating composition in the form of a powder having an average particle size of about 10 to 300 microns comprising:
(1) a semi-crystalline polyester having a glass transition temperature of not more than 50° C., a number average molecular weight of about 500 to 10,000, a hydroxyl number of about 5 to 200 and an inherent viscosity of about 0.1 to 0.5 and comprised of:
(a) diacid residues comprised of at least 80 mole percent of terephthalic acid residues, 1,4-cyclohexanedicarboxylic acid residues, 1,3-cyclohexanedicarboxylic acid residues or a mixture thereof; and
(b) diol residues comprised of (i) about 50 to 100 mole percent of residues having the formula —O(CH$_2$)$_n$O— wherein n is about 6 to 12 and (ii) about 0 to 50 mole percent of 2,2-dimethyl-1,3-propanediol residues provided that at least 90 mole percent of the diol residues are residues having the formula —O(CH$_2$)$_n$O— and 2,2-dimethyl-1,3-propanediol residues; and (2) a cross-linking effective amount of at least one oxime-blocked polyisocyanate which is the reaction product of an oxime selected from 2,4-dimethyl-3-pentanone oxime and 2,6-dimethyl-4-heptanone oxime and a polyisocyanate selected from the trimer of isophorone diisocyanate, methylenebis(4,4'-cyclohexylisocyanate), 1,3-bis(1-isocyanato-1-methylethyl)benzene and 1,4-bis(1-isocyanato-1-methylethyl)benzene.

13. A thermosetting coating composition according to claim 12 containing a cross-linking catalyst and a flow aid.

14. A thermosetting powder coating composition according to claim 12 having an average particle size of about 15 to 75 microns comprising:
(1) a semi-crystalline polyester having a glass transition temperature of less than 20° C., a melting point of about 90° to 140° C., a hydroxyl number of about 8 to 60 and an inherent viscosity of about 0.1 to 0.4 comprised of:
  (a) diacid residues consisting essentially of about 50 to 100 mole percent terephthalic acid residues and 0 to about 50 mole percent 1,4-cyclohexanedicarboxylic acid residues, 1,3-cyclohexanedicarboxylic acid residues or a mixture thereof; and
  (b) diol residues consisting essentially of about 70 to 100 mole percent of residues having the formula —O(CH$_2$)$_n$O— wherein n is about 6 to 12 and about 0 to 30 mole percent 2,2-dimethyl-1,3-propanediol residues, and
(2) about 8 to 25 weight percent, based on the weight of (1) and (2), of an oxime-blocked polyisocyanate compound which is the reaction product of an oxime selected from 2,4-dimethyl-3-pentanone oxime and 2,6-dimethyl-4-heptanone oxime and the trimer of isophorone diisocyanate.

15. A thermosetting coating composition according to claim 14 containing a cross-linking catalyst and a flow aid.

16. A thermosetting powder coating composition according to claim 12 having an average particle size of about 15 to 75 microns comprising:
(1) a semi-crystalline polyester having a glass transition temperature of less than 20° C., a melting point of about 90° to 140° C., a hydroxyl number of about 8 to 60 and an inherent viscosity of about 0.1 to 0.4 comprised of:
  (a) diacid residues consisting essentially of about 50 to 100 mole percent terephthalic acid residues and 0 to about 50 mole percent 1,4-cyclohexanedicarboxylic acid residues, 1,3-cyclohexanedicarboxylic acid residues or a mixture thereof; and
  (b) diol residues consisting essentially of about 70 to 100 mole percent of residues having the formula —O(CH$_2$)$_n$O— wherein n is about 6 to 12 and about 0 to 30 mole percent 2,2-dimethyl-1,3-propanediol residues, and
(2) about 8 to 25 weight percent, based on the weight of (1) and (2), of an oxime-blocked polyisocyanate compound having the formula:

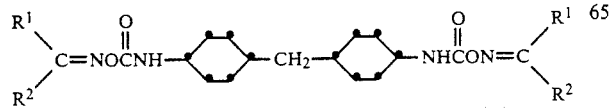

-continued

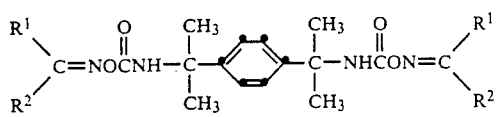

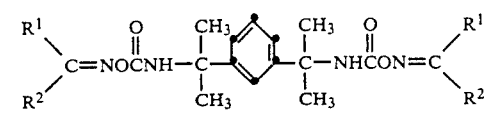

wherein R$^1$ and R$^2$ each is isopropyl or isobutyl.

17. A thermosetting coating composition according to claim 16 containing a cross-linking catalyst and a flow aid.

18. A thermosetting coating composition in the form of a powder having an average particle size of about 10 to 300 microns comprising:
(1) about 50 to 90 weight percent, based on the weight of (1) and (2) of a semi-crystalline polyester having a glass transition temperature of not more than 50° C., a number average molecular weight of about 500 to 10,000, a hydroxyl number of about 20 to 200 and an inherent viscosity of about 0.1 to 0.5 and comprised of:
  (a) diacid residues comprised of at least 80 mole percent of terephthalic acid residues, 1,4-cyclohexanedicarboxylic acid residues or a mixture thereof; and
  (b) diol residues comprised of (i) about 50 to 100 mole percent of residues having the formula —O(CH$_2$)$_n$O— wherein n is about 6 to 12 and (ii) about 0 to 50 mole percent of 2,2-dimethyl-1,3-propanediol residues, provided that at least 90 mole percent of the diol residues are residues having the formula —O(CH$_2$)$_n$O— and 2,2-dimethyl-1,3-propanediol residues;
(2) about 50 to 10 weight percent, based on the weight of (1) and (2), of one or more amorphous polyesters having a glass transition temperature of greater than 40° C., a hydroxyl number of about 20 to 200 and an inherent viscosity of about 0.1 to 0.5; and
(3) a cross-linking effective amount of at least one oxime-blocked polyisocyanate which is the reaction product of an oxime selected from 2,4-dimethyl-3-pentanone oxime and 2,6-dimethyl-4-heptanone oxime and a polyisocyanate selected from the trimer of isophorone diisocyanate, methylenebis(4,4'-cyclohexylisocyanate), 1,3-bis(1-isocyanato-1-methylethyl)benzene and 1,4-bis(1-isocyanato-1-methylethyl)benzene.

19. A thermosetting powder coating composition according to claim 18 having an average particle size of about 15 to 75 microns comprising:
(1) about 50 to 90 weight percent, based on the weight of (1) and (2), of a semi-crystalline polyester having a glass transition temperature of less than 20° C., a melting point of about 90° to 140° C., a hydroxyl number of about 8 to 60 and an inherent viscosity of about 0.1 to 0.4 comprised of: (a) diacid residues consisting essentially of about 50 to 100 mole percent terephthalic acid residues and 0 to about 50 mole percent 1,4-cyclohexanedicarboxylic acid residues, 1,3-cyclohexanedicarboxylic acid residues or a mixture thereof; and (b) diol residues consisting essentially of about 70 to 100 mole percent of residues having the formula —O(CH$_2$)$_n$O— wherein n is about 6 to 12 and about 0 to 30 mole percent 2,2-dimethyl-1,3-propanediol residues; (2) about 50 to 10 weight percent, based on the weight of (1) and (2), of one or more amorphous polyester having a glass transition temperature of greater than 55° C., a hydroxyl number of about 25 to 80, an acid number of not more than 15 and an inherent viscosity of about 0.10 to 0.4 comprised of: (a) diacid residues of which at least 50 mole percent are terephthalic acid residues; (b) diol residues of which at least 50 mole percent are 2,2-dimethyl-1,3-propanediol residues; and (c) up to 15 mole percent, based on the total moles of (b) and (c), of trimethylolpropane residues; and (3) about 8 to 25 weight percent, based on the weight of (1), (2) and (3), of an oxime-blocked polyisocyanate compound which is the reaction product of an oxime selected from 2,4-dimethyl-3-pentanone oxime and 2,6-dimethyl-4-heptanone and the trimer of isophorone diisocyanate.

20. A thermosetting powder-coating composition according to claim 19 having an average particle size of about 15 to 50 microns wherein the amorphous polyester has a glass transition temperature (Tg) of about 55° to 65° C., a hydroxyl number of about 35 to 65, an acid number of not more than 10 and an inherent viscosity of about 0.10 to 0.25 and consisting essentially of terephthalic acid residues, 2,2-dimethyl-1,3-propanediol residues and up to 15 mole percent, based on the total moles of trimethylolpropane and 2,2-dimethyl-1,3-propanediol residues, of trimethylolpropane residues.

21. A thermosetting powder coating composition in the form of a powder having an average particle size of about 15 to 50 microns comprising:
(1) about 50 to 90 weight percent, based on the weight of (1) and (2), of a semi-crystalline polyester having a glass transition temperature of less than 20° C., a melting point of about 90° to 140° C., a hydroxyl number of about 8 to 60 and an inherent viscosity of about 0.1 to 0.4 comprised of:
  (a) diacid residues consisting essentially of about 50 to 100 mole percent terephthalic acid residues and 0 to about 50 mole percent 1,4-cyclohexanedicarboxylic acid residues, 1,3-cyclohexanedicarboxylic acid residues, or a mixture thereof; and
  (b) diol residues consisting essentially of about 70 to 100 mole percent of residues having the formula —O(CH$_2$)$_n$O— wherein n is about 6 to 12 and about 0 to 30 mole percent 2,2-dimethyl-1,3-propanediol residues;
(2) about 50 to 10 weight percent, based on the weight of (1) and (2), of one or more amorphous polyesters having a glass transition temperature of about 55° to 65° C., a hydroxyl number of about 35 to 65, an acid number of not more than 10 and an inherent viscosity of about 0.10 to 0.25 and consisting essentially of terephthalic acid residues, 2,2-dimethyl-1,3-propanediol residues and up to 15 mole percent, based on the total mole of trimethylolpropane and 2,2-dimethyl-1,3-propanediol residues, of trimethylolpropane residues;
(3) about 8 to 25 weight percent, based on the weight of (1), (2) and (3), of an oxime-blocked polyisocyanate compound which is the reaction product of an oxime selected from 2,4-dimethyl-3-pentanone oxime and 2,6-dimethyl-4-heptanone and the trimer of isophorone diisocyanate;
(4) an acrylic polymer flow aid; and
(5) a cross-linking catalyst selected from organo-tin compounds.

22. An article coated with the reaction product of a composition comprising:
(1) a semi-crystalline polyester having a glass transition temperature of not more than 50° C., a number average molecular weight of about 500 to 10,000, a hydroxyl number of about 20 to 200 and an inherent viscosity of about 0.1 to 0.5 and comprised of:
  (a) diacid residues comprised of at least 80 mole percent of terephthalic acid residues, 1,4-cyclohexanedicarboxylic acid residues, 1,3-cyclohexanedicarboxylic acid residues or a mixture thereof; and
  (b) diol residues comprised of (i) about 50 to 100 mole percent of residues having the formula —O(CH$_2$)$_n$O— where n is about 6 to 12 and (ii) about 0 to 50 mole percent of 2,2-dimethyl-1,3-propanediol residues, provided that at least 90 mole percent of the diol residues are residues having the formula —O(CH$_2$)$_n$O— and 2,2-dimethyl-1,3-propanediol residues; and
(2) a cross-linking effective amount of at least one oxime-blocked polyisocyanate which is the reaction product of an oxime selected from 2,4-dimethyl-3-pentanone oxime and 2,6-dimethyl-4-heptanone oxime and a polyisocyanate selected from the trimer of isophorone diisocyanate, methylene-bis(4,4-cyclohexylisocyanate), 1,3-bis(1-isocyanato-1-methylethyl)benzene and 1,4-bis(1-isocyanato-1-methylethyl)benzene.

23. An article coated with the reaction product of a composition comprising:
(1) about 50 to 90 weight percent, based on the weight of (1) and (2), of a semi-crystalline polyester having a glass transition temperature of not more than 50° C., a number average molecular weight of about 500 to 10,000, a hydroxyl number of about 5 to 200 and an inherent viscosity of about 0.1 to 0.5 and comprised of:
  (a) diacid residues comprised of at least 80 mole percent of terephthalic acid residues, 1,4-cyclohexanedicarboxylic acid residues, 1,3-cyclohexanedicarboxylic acid residues or a mixture thereof; and
  (b) diol residues comprised of (i) about 50 to 100 mole percent of residues having the formula —(CH$_2$)$_n$O— wherein n is about 6 to 12 and (ii) about 0 to 50 mole percent of 2,2-dimethyl-1,3-propanediol residues, provided that at least 90 mole percent of the diol residues are residues having the formula —(CH$_2$)$_n$O— and 2,2-dimethyl-1,3-propanediol residues;
(2) about 50 to 10 weight percent, based on the weight of (1) and (2), of one or more amorphous polyesters having a glass transition temperature of greater than 40° C., a hydroxyl number of about 20 to 200 and an inherent viscosity of about 0.1 to 0.5; and
(3) a cross-linking effective amount of at least one oxime-blocked polyisocyanate which is the reaction product of an oxime selected from 2,4-dimethyl-3-pentanone oxime and 2,6-dimethyl-4-heptanone oxime and a polyisocyanate selected from the trimer of isophorone diisocyanate, methylene-bis(4,4'-cyclohexylisocyanate), 1,3-bis(1-isocyanato-1-methylethyl)benzene and 1,4-bis(1-isocyanato-1-methylethyl)benzene.

* * * * *

UNITED STATES PATENT AND TRADEMARK OFFICE
CERTIFICATE OF CORRECTION

PATENT NO. : 5,028,682

DATED : July 2, 1991

INVENTOR(S) : J. Stewart Witzeman, Glenn C. Jones

It is certified that error appears in the above-identified patent and that said Letters Patent is hereby corrected as shown below:

Title page, item [54] and in column 1:
The title should read ---OXIME-BLOCKED POLYISOCYANATES AND POLYESTER AND POWDER COATING COMPOSITIONS CONTAINING SUCH OXIME-BLOCKED POLYISOCYANATES---.

Column 18, line 39, "thyl3-pentanone" should be ---thyl-3-pentanone---.

Column 19, line 14, "$R_1$ and $R_2$" should be ---$R^1$ and $R^2$---.

line 50, the "," after "hydroxyl" should be deleted.

Column 21, line 53, "Claim 17" should be ---Claim 7---.

Column 22, line 13, after "2,2-dimethyl-1,3-propanediol" insert ---residues; and---.

Column 25, line 60, "mole" (2nd Occurence) should be---moles---.

Signed and Sealed this

Eighth Day of December, 1992

Attest:

DOUGLAS B. COMER

Attesting Officer

Acting Commissioner of Patents and Trademarks